United States Patent
Balchin et al.

(10) Patent No.: US 10,210,469 B2
(45) Date of Patent: Feb. 19, 2019

(54) SUPPORT FOR REQUIREMENTS OF PEOPLE IN A PUBLIC SITE OR VENUE

(71) Applicant: INTERNATIONAL BUSINESS MACHINES CORPORATION, Armonk, NY (US)

(72) Inventors: Ann K. Balchin, Rome (IT); Susanna Baldi, Rome (IT); Cristina Bonanni, Rome (IT); Audrey D. Borden, San Rafael, CA (US); Timothy I. Brown, Austin, TX (US); Giuseppe Longobardi, Naples (IT); Gabriella Santoro, Rome (IT); Lisa Marie Towles, Oakland, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/907,965

(22) Filed: Feb. 28, 2018

(65) Prior Publication Data
US 2019/0026673 A1    Jan. 24, 2019

Related U.S. Application Data

(63) Continuation of application No. 15/655,363, filed on Jul. 20, 2017.

(51) Int. Cl.
*G06Q 10/06* (2012.01)
*H04W 4/80* (2018.01)
(Continued)

(52) U.S. Cl.
CPC ....... *G06Q 10/06315* (2013.01); *G16H 10/65* (2018.01); *G16H 40/20* (2018.01); *H04W 4/021* (2013.01); *H04W 4/80* (2018.02)

(58) Field of Classification Search
CPC .. G06Q 10/06315; G06Q 50/22; G06Q 50/24; G16H 4/20; G16H 10/65;
(Continued)

(56) References Cited

U.S. PATENT DOCUMENTS 8,044,772 B1   10/2011 Roe
8,441,356 B1    5/2013 Tedesco et al.
(Continued)

FOREIGN PATENT DOCUMENTS

DE           10304073 A1    9/2004

OTHER PUBLICATIONS

Aly, "MNDWSN for Helping People with Different Disabilities", Research Article, International Journal of Distributed Sensor Networks, vol. 2014, Article ID 489289, 7 pages.
(Continued)

*Primary Examiner* — Dylan C White
(74) *Attorney, Agent, or Firm* — Michael A. Petrocelli

(57) ABSTRACT

A computer-implemented method and system for supporting a person at a site, venue, or location where the person may have a requirement. The method and system include storing a requirement code in a handheld device, and storing the requirement code and at least one characteristic relating to the requirement code in a requirement certification database. The requirement code is transmitted from the handheld device to a sensor at the site, and action data is received by a facility of the site from the requirement certification database. The action data is indicative of an action to be performed by the facility, dependent on the requirement code and the at least one characteristic, such that the facility adapts its function to a requirement of the person having the requirement.

1 Claim, 6 Drawing Sheets

(51) Int. Cl.
*H04W 4/021* (2018.01)
*G16H 40/20* (2018.01)
*G16H 10/65* (2018.01)

(58) Field of Classification Search
CPC ......... H04W 4/20; H04W 10/65; G06F 19/30; G06F 19/32; G06F 19/34
USPC ...................................................... 705/7.25
See application file for complete search history.

(56) References Cited

U.S. PATENT DOCUMENTS

| | | | | |
|---|---|---|---|---|
| 8,494,507 | B1* | 7/2013 | Tedesco | A61F 4/00 434/112 |
| 9,377,922 | B2 | 6/2016 | Work | |
| 9,826,049 | B2* | 11/2017 | Lim | H04L 67/18 |
| 2003/0043044 | A1 | 3/2003 | Hunter | |
| 2005/0099291 | A1* | 5/2005 | Landau | A61H 3/061 340/539.13 |
| 2006/0129308 | A1* | 6/2006 | Kates | A61H 3/061 701/532 |
| 2008/0318563 | A1* | 12/2008 | Ross | G06F 19/322 455/418 |
| 2011/0201319 | A1* | 8/2011 | Ait Hamouda | H04W 4/02 455/414.1 |
| 2013/0090965 | A1* | 4/2013 | Rivere | G06Q 10/06311 705/7.15 |
| 2013/0124523 | A1* | 5/2013 | Rogers | G06F 19/32 707/737 |
| 2013/0238349 | A1* | 9/2013 | Sethumadhavan | G06Q 50/24 705/2 |
| 2014/0181673 | A1* | 6/2014 | Work | G06F 3/0484 715/729 |
| 2017/0099575 | A1* | 4/2017 | Schulz | G06Q 10/06315 |
| 2017/0111770 | A1* | 4/2017 | Kusens | G01S 1/68 |
| 2018/0168459 | A1* | 6/2018 | Tran | H04B 1/3827 |
| 2018/0214051 | A1* | 8/2018 | Larson | G16H 50/20 |
| 2018/0276365 | A1* | 9/2018 | D'Alterio | G06F 21/36 |

OTHER PUBLICATIONS

Baldwin, "6 Glasses with Integrated Displays That You Can Buy Today", Wired, GEAR, Apr. 11, 2012, pp. 1-10, https://www.wired.com/2012/04/6-glasses-with-integrated-displays-that-you-can-buy-today/.

Barnwell, "The Smartphone You Can Wear Like a Bracelet", Digitaltrends, Wearables, Jun. 4, 2015, pp. 1-4, https://www.digitaltrends.com/wearables/the-smartphone-you-can-wear-like-a-bracelet/#:si47wISOUfQGnA.

Hdblog.it, "Il primo smartphone flessibile é realtá", Apr. 26, 2016, pp. 1-5, http://android.hdblog.it/2016/04/26/primo-smartphone-flessibile-realta/.

CARE—Medical History Bracelet, printed on Dec. 23, 2016, pp. 1-3, http://medicalhistorybracelet.com/.

Patil et al., "A Generic Information Service Framework for Physically Challenged People in Wireless Networks", International Journal of Computer and Electrical Engineering, vol. 3, Aug. 2011, pp. 469-472.

Schwartz, "Siemens to pilot RFID bracelets for health care", InfoWorld, Jul. 23, 2004, pp. 1-3.

TAP2TAG, "Medical Alert RFID Bracelets, Keyfobs, Cards and Stickers", printed on Dec. 23, 2016, pp. 1-4, https://www.tap2tag.me/shop/medical-tags.html.

Varghese, "Application of IoT to improve the life style of differently abled people", IOSR Journal of Computer Engineering (IOSR-JCE), International Conference on Emerging Trends in Engineering & Management, (ICETEM-2016), pp. 29-34.

Mell et al., "The NIST Definition of Cloud Computing", Recommendations of the National Institute of Standards and Technology, Special Publication 800-145, Sep. 2011, 7 pages.

Pending U.S. Appl. No. 15/655,363, filed Jul. 20, 2017, entitled: "Support for Requirements of People in a Public Site or Venue", pp. 1-35.

IBM: List of IBM Patents or Patent Applications Treated as Related (Appendix P), Apr. 9, 2018, pp. 1-2.

* cited by examiner

SUPPORT FOR REQUIREMENTS OF PEOPLE IN A PUBLIC SITE OR VENUE

FIELD

The invention relates generally to a method for supporting people with a requirement or need, and more specifically, to a computer-implemented method for supporting a person having a requirement or need, such as a disability, at a site, venue, or location. The invention relates further to a related system for supporting a person having a requirement, which can include access, services, preferences, a disability or a handicap, or other types or examples of particular or specified needs, conditions, or preferences at a site, venue, or location.

BACKGROUND

The collaboration of science and technology has attempted to improve the functionality, usability, and efficiency of "adaptive" tools intended for use by persons with special or different needs, such as persons with different disabilities. The digitization and the Internet-of-Things has provided and may continue to provide a large plurality of sensors everywhere—in particular, sensor equipped facilities—allow a new approach to support people having requirements, special or different needs, or having disabilities. It may also help to overcome a common and persistent problem among typical communities, including: getting assistance in a proactive way for people with specific requirements, which can include people with disabilities. There are currently very few mechanisms in place by which a disabled person can initiate identification when reaching a public location or venue, and that may allow the person with requirements to communicate their need, or their disability to obtain real-time specific support and assistance.

The currently available systems are neither proactive nor automatic. Furthermore, they may not be available on demand in associating the set of appropriate support actions to a specific requirement, such as a specific disability or specific need.

SUMMARY

The proposed solutions herein are described by the independent claims, in particular:

According to one aspect of the present invention, a computer implemented method for supporting a person at a site, the person having a requirement, may be provided. The method may comprise storing a requirement code in a handheld device, storing the requirement code and at least one characteristic relating to the requirement code in a requirement certification database, transmitting the requirement code from the handheld device to a sensor at the site and, receiving action data by a facility of the site from the requirement certification database. The action data may be indicative of an action to be performed by the facility, dependent on the requirement code and the at least one characteristic such that the facility adapts its function to a requirement of the person having the requirement.

According to another aspect of the present invention, a related system for supporting a person at a site, the person having a requirement, may be provided. The system may comprise a handheld device adapted for storing a requirement code, a requirement certification database unit adapted for storing the requirement code and at least one characteristic relating to the requirement code, a sensor at the public site adapted for receiving the requirement code from the handheld device and, a receiver adapted for receiving action data by a facility of the site from the requirement certification database The action data may be indicative of an action to be performed by the facility dependent on the requirement code and the at least one characteristic such that the facility adapts its function to a requirement of the person having the requirement.

Furthermore, embodiments may take the form of a related computer program product, accessible from a computer-usable or computer-readable medium providing program code for use, by or in connection with a computer or any instruction execution system. For the purpose of this description, a computer-usable or computer-readable medium may be any apparatus that may contain means for storing, communicating, propagating or transporting the program for use, by or in a connection with the instruction execution system, apparatus, or device.

BRIEF DESCRIPTION OF THE SEVERAL VIEWS OF THE DRAWINGS

It should be noted that embodiments of the invention are described with reference to different subject-matters. In particular, some embodiments are described with reference to method type claims whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above and further aspects of the present invention are apparent from the examples of embodiments to be described hereinafter and are explained with reference to the examples of embodiments, but to which the invention is not limited.

Figure 1:
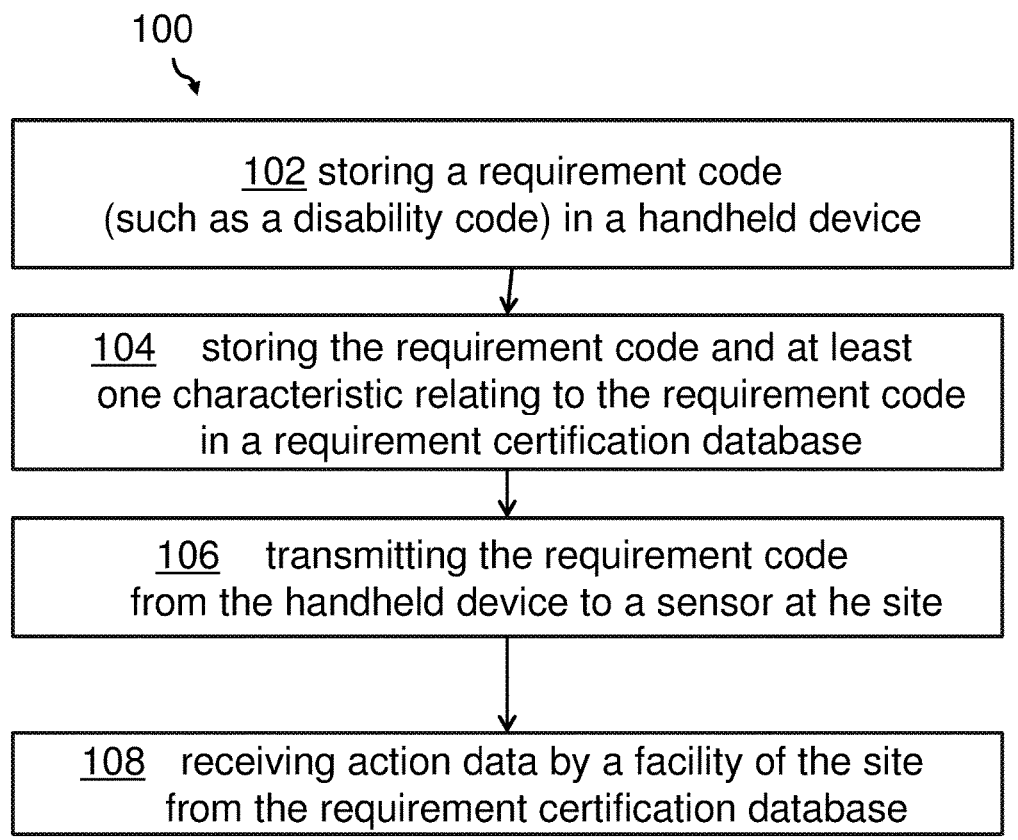
Figure 2:
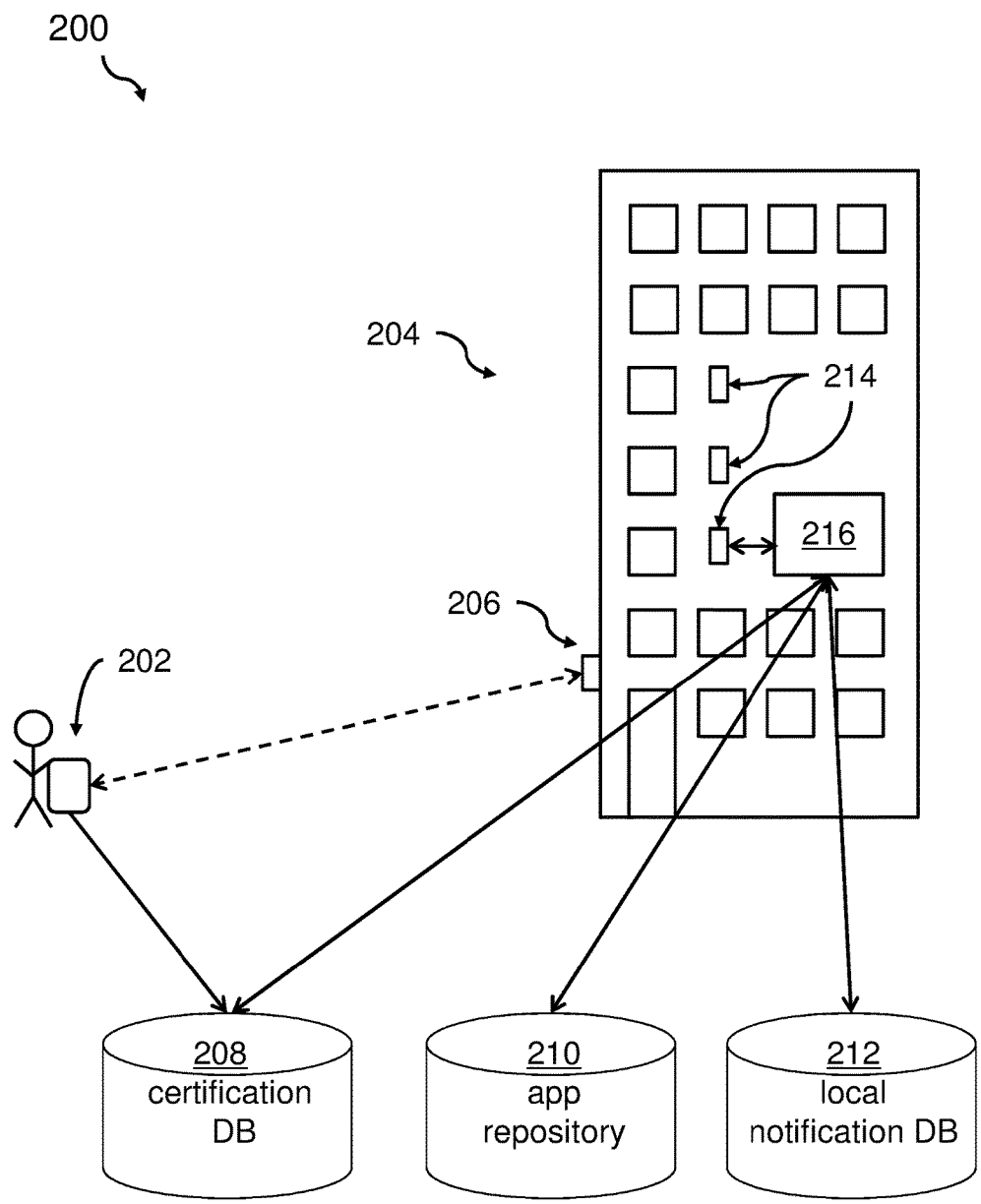
Figure 3:
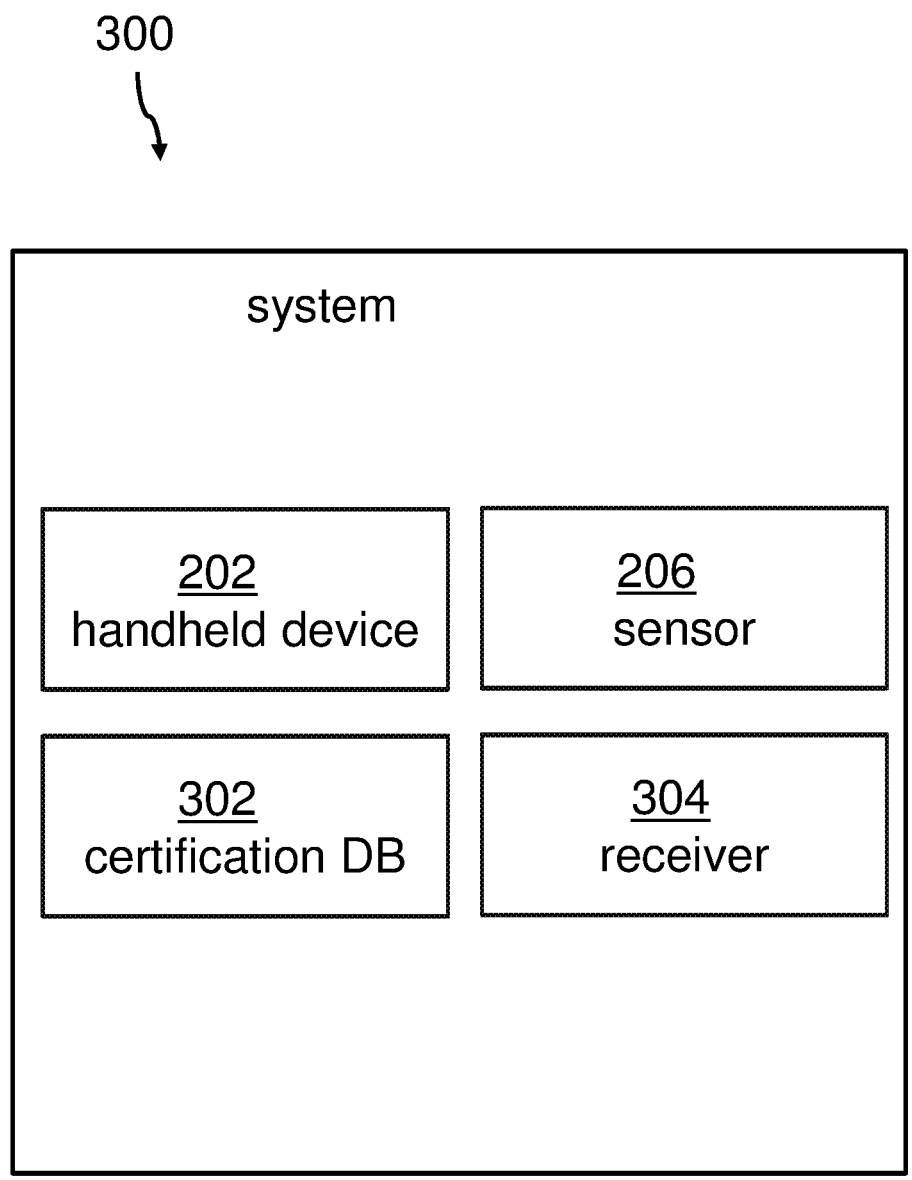
Figure 4:
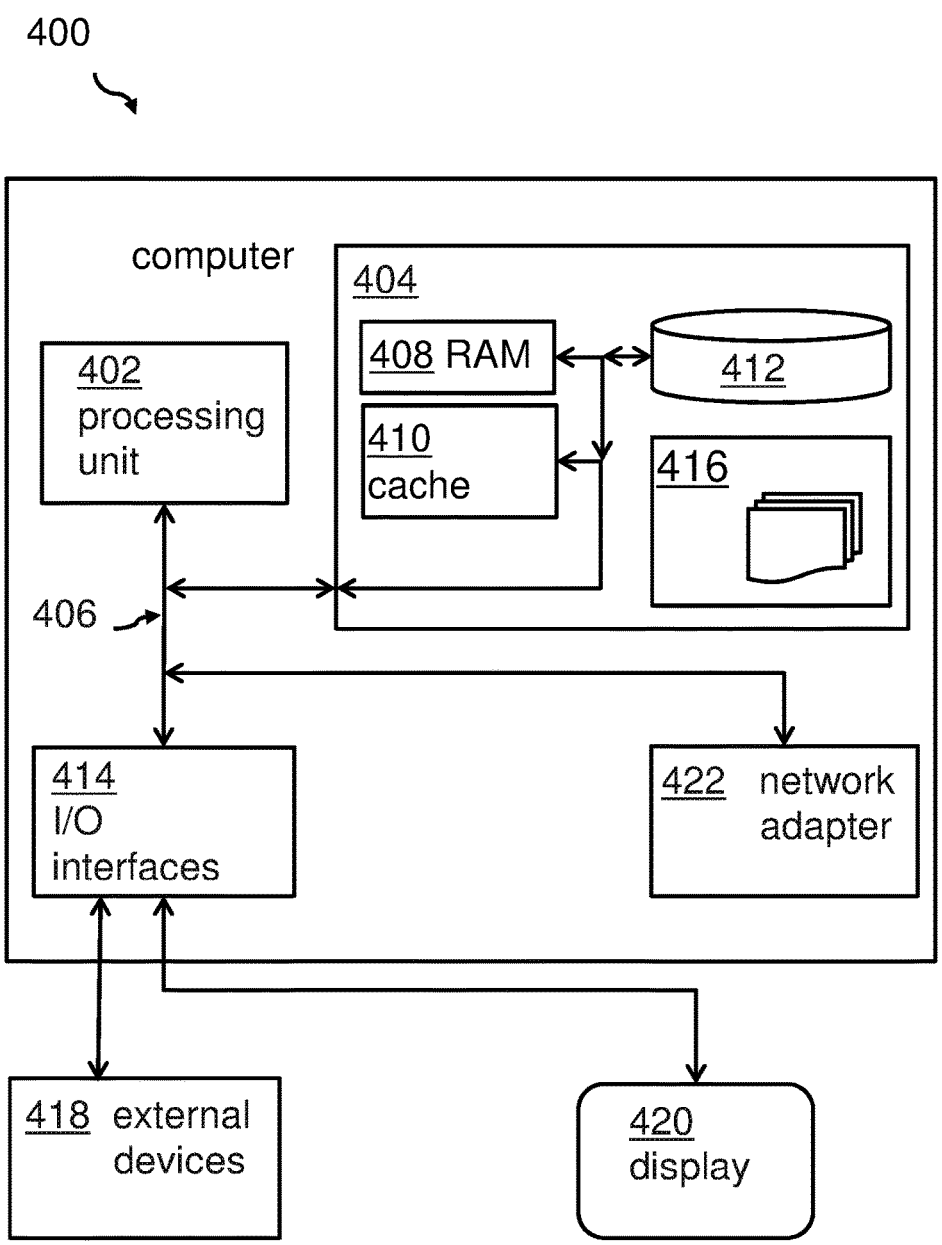
Figure 5:
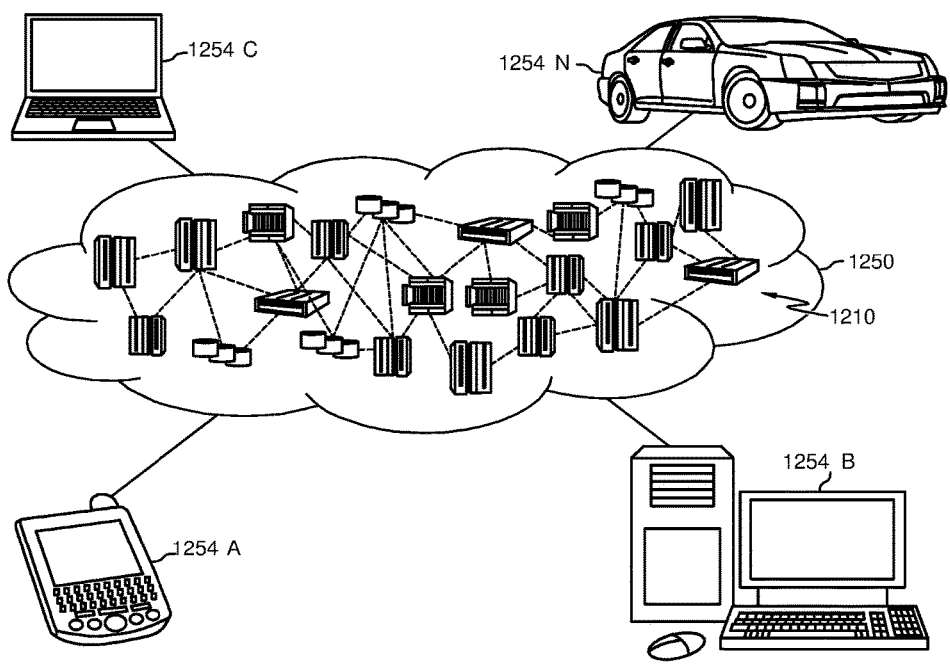
Figure 6:
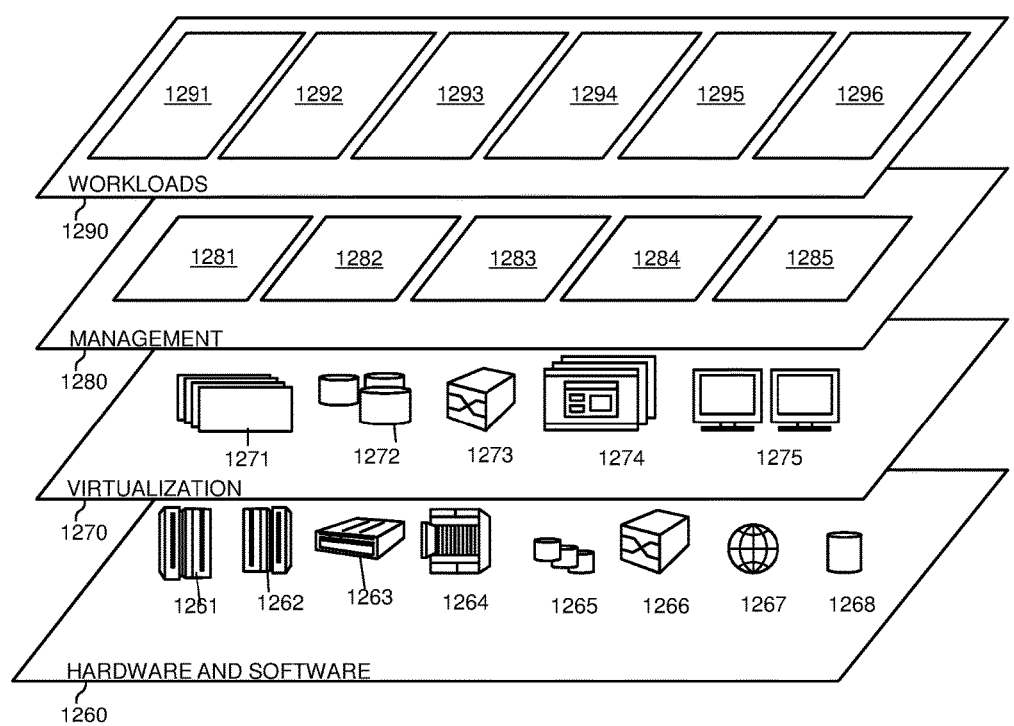

Preferred embodiments of the invention will be described, by way of example only, and with reference to the following drawings:

FIG. 1 shows a block diagram of an embodiment of the inventive computer implemented method for supporting a person at a site, the person having a requirement;

FIG. 2 shows a block diagram of an embodiment of a set-up of involved components;

FIG. 3 shows a block diagram of an embodiment of a system in an overview form;

FIG. 4 shows an embodiment of a computing system usable with the method and system;

FIG. 5 depicts a cloud computing environment according to an embodiment of the present invention; and FIG. 6 depicts abstraction model layers according to an embodiment of the present invention.

DETAILED DESCRIPTION

In the context of this description, the following conventions, terms and/or expressions may be used:

The term 'site' may denote any geographical location to which people may have access, e.g., a venue or a location. The site may, in particular be a public site, like any open-air site, or any building accessible by people. The building may, in particular, be a public building like a public administration office, a university, a school, a kindergarten, a museum, a shopping center, a restaurant, an exhibit, and the like.

The term 'requirement code' may denote a code comprising alphanumerical characters and/or digital values, describing a requirement a person may have in a standardized and encoded manner. One requirement code may relate to a plurality of people having the requirement code.

The term 'disability code' may denote a code comprising alphanumerical characters and/or digital values, describing a disability a person may have in a standardized and encoded manner. One disability code may relate to a plurality of disabled or handicapped people.

The term 'handheld device' may denote any device a person may carry around. The device may have included a transceiver for wireless communication. The sender component of the transceiver may be individually and selectively activated. In particular, the sender for sending the disability code may be selectively activatable. The handheld device may comprise a screen, an input field (smart touchpad) and audio in and output. The handheld device may also comprise text-to-speech translation capabilities.

The term 'characteristic' may denote a specific inability relating to the requirement code, such as a disability code and/or special needs a person may have. The characteristic maybe referred to by means of a code.

The term 'requirement certification database' may denote a database local to a site, e.g., a public site, for storing the requirement code of a person, in one instance a 'disability certification database' may denote a database local to a site, e.g., a public site, for storing a disability code of a person. The requirement certification database may be operated in a trusted manner, i.e., with precautions regarding data security and data privacy. The data in the database may only be accessible using individual credentials and the data may be stored in an encoded form.

The term 'sensor' may denote any receiver adapted for receiving data from a handheld device. Thus, the sensor may be connected to or be integrated into a mobile public communication network (e.g., mobile telephone network). Alternatively, the sensor may be adapted for only receiving data from the handheld device from shorter distances, e.g., the reach of a wireless local area network (WLAN according to e.g., IEEE 802.11), Bluetooth (e.g., according to IEEE 802.15.1; Bluetooth® 4.0, 4.1, 4.2 or higher), or NFC (near field communication according to, e.g., ISO/IEC 18000-3 air interface).

The term 'action data' may denote data usable to control the function of a facility at a site, e.g., a public site.

The term 'facility' may denote any technical equipment or organizational provision by which a building or another site may change its functionality; e.g., an activation of an elevator, an opening of a door (e.g., only used by people with a disability), an arrangement for a fast lane, and so on.

The term 'adapts its function' may denote that a site, like a public building, may adapt its facilities in a way such that people with a requirement (such as a disability) may be supported in a better way or supported at all. If, e.g., people at the site use stairs normally to go from one level to another, an "adaption of its function" may comprise activating an elevator dedicated to help people with disabilities to go from one level to another.

The term 'trusted data center' may denote that the datacenter operates under special conditions guaranteeing a high level of data security and privacy.

The proposed computer implemented method for supporting a person at a site, the person having a requirement (such as a disability) may offer multiple advantages and technical effects:

The proposed methods and concepts may increase the quality of life of people having special or different needs or requirements, or having disabilities or a handicap. In one instance, according to the embodiment of the disclosure, people-specific assistance may be made available in an automatic and proactive way. In another instance, the person having the requirement may decide themselves whether knowledge is given to systems potentially be designed to recognize a signal indicative of the requirement of the person, such as a disability or a special need. Thus, the message comprising the requirement code may or might not be send from the handheld device to the sensor of a site.

Additionally, the person with a requirement, such as a handicapped person might also wear a smart band around his wrist (or somewhere else) which may have a good visibility by other people on site. The smart band may begin to emit a light according to the specific requirement code, such as a disability code. This way, other people on site may recognize the requirement for special requirement. The illumination may also or instead be integrated into an outer frame of a smartphone, carried visibly, or any other device designed for signaling people with or caring for a person with a requirement. However, the signals may be switchable.

An example may illustrate this, for example, for a person needing a wheelchair it may be obvious that the disability—lacking the ability of walking around without a wheelchair—is visible and recognizable by other people in the environment. However, people having an illness, not directly visible, visiting a public site and needing assistance in order to navigate the public site may not want that everybody in the public site may recognize the disability which is not readily apparent.

The here proposed methods and systems are designed to support both scenarios and organize assistance for the person with a requirement in an appropriate manner adapted to the specific requirement. It may either be organized in the form of personal assistance or automatically available technical assistance, e.g., specific navigational support on site or the on demand opening of an express lane for people with disabilities on demand.

Furthermore, the site management and/or the technical systems on site may adapt proactively to the arrival of a person having disabilities. All of this may be coordinated by a standardized disabilities certification database as central information hub which may be managed site-specific or for a usage by a plurality of different sites. The following examples may render the here described advantages and technical effects more transparently:

Example A) Fire Emergency

A real-time use might be related to emergency services. For example: If a fire breaks out, the firefighters may need to be aware that there are persons with disabilities in the venue, and what type of disability they have. For example: If a firefighter were to shout "is anyone here?" a hearing or speaking impaired person would not be able to answer and would therefore be in danger of not receiving assistance. The proposed method and system may enable a speech-to-text translation and the person may receive a related message.

Or, knowing in advance that a person cannot walk, firefighters may arrive prepared with the appropriate means of transport.

Example B) Museum

For example: If a person has a sight disability, when entering a museum at a certain established place, the smart device of the user may automatically be detected and the person may be identified along with his/her disability. A text-to-speech program may be started by the handheld device, which may send an audio guide with instructions to the smart phone or smart watch owned by the disabled person, which may be recognized through a connected earpiece. Also, based on the type of disability, the museum system may start tracking the location of the device and may provide instructions about how to move around, as well as providing a list of special facilities available and the way to reach them, according to accommodations needed. No description may need to be actually downloaded onto the device, but it may be sent real-time in streaming mode. The smart device may also easily be visible to people around, including stewards or hostesses who may intercept, through their own devices the presence of a person having a requirement or a specific requirement, such as a disabled person, and may provide assistance directly if required.

Example C) Cinema

If, instead, a person may have a hearing disability, the device may be detected when the person may enter a cinema and a speech-to-text app may be started on a smart device—e.g., a smartphone—that may allow reading the movie dialogs on the screen. If the person may also have glasses that include a head-up display, the person may watch the movie with the subtitle projected directly on the glasses, as if they were on the cinema screen.

Example D) Shopping Center

Another use of the proposed method and system might be to send the disabled person real-time warnings. Assumed, the disability may be movement-related; when the disabled person may approach a parking area of a shopping center, the device may be detected and connected to a related backend system. The system may inform the disabled person to use a specific entrance—e.g., the north entrance—instead of the south entrance because the south elevator may be closed for maintenance, or to park in an alternative location if the primary parking access has no elevator enabled to carry wheelchairs. Additionally it may also it warn the disabled person to avoid, e.g., the left side of the 2nd floor, which may currently be cleaned and might be wet. The system may also inform about a restoration of normal conditions.

Example E) Restaurant

If a person that may suffer from a celiac disease or an allergy to specific foods may arrive at a restaurant, the application running on a handheld device—e.g., a smart watch that may communicate the identity their requirements related to their disease or allergy, and the person may receive a customized menu for their specific dietary restrictions. Or if the restaurant has an electronic menu, the list would automatically exclude all the items that a person having requirements, such as dietary requirement, is not allowed to eat (or would identify which ones aren't suitable).

Example F) Site Planning for Disabilities

The person with a disability, when booking a visit to a specific venue such as a museum, shopping center, restaurant, or exhibit, may have the option of specifying in advance their needs and what they intend to do at the venue. For example, a blind person may communicate their itinerary within a museum so that the museum can arrange personalized assistance based on that itinerary and disability (the museum might have some areas that cannot be reached easily by a person with a specific disability).

Example G) Car Park Priority

When driving into a parking lot (e.g., of a shopping center or of a cinema or of a museum, etc.), where there are parking spaces reserved to the cars of people with disabilities, the handheld device may also register with the sensor of the site during approaching the parking lot. This allow an easy access to a reserved parking lot entrance or area. The gate to such area may be opened automatically (alternatively, a "green light" may be switched on signaling an access allowing for the disabled parking area). This way, a protection of the disabled parking spaces is possible and the people having the disability have a reserved parking area. Unauthorized cars may be removed easily.

In the following, more embodiments of the method—which may also be applicable for the system—are described.

According to one preferred embodiment of the method, the handheld device may be selected out of the group comprising a smartphone, a smartwatch, a tablet computer, a dedicated disability system, a wheelchair, smart glasses and, a smart bracelet (smart band). Thus, basically any handheld device may be usable for the purpose of the here proposed concept. The handheld device may be only enabled to transmit a requirement code. Additional functions, like receiving navigational maps for the site reflecting the specifics of the site or text-to-speech translation in view of a certain requirement, may be optional.

According to one advantageous embodiment, the method may also comprise receiving, by the handheld device, site-specific data about a temporary impediment or a safety restriction of the site as a reaction to the receiving the requirement code by the sensor of the site. The received site-specific data may be selected according to requirements defined in the action data. Thus, a person with the disability may receive pre-warnings about a restrictive use of facilities of the site, e.g., an elevator having a defect or being unsuitable, such that a certain pathway may be blocked for a person using a wheelchair. Or, a hallway may be blocked entirely so it may not be usable by any person. Receiving this kind of information may in particular be useful for a person having certain requirements, such as a handicapped person or a person with a disability, and which requires some sort of particular accommodation or service.

According to one embodiment of the method, the disability certification database may store action data for one or for more sites. Thus, the disability certification database may hold only reference data relating the disability code to a more detailed description of potential disabilities, as well as requirements, a person with a disability may have. Alternatively, the disability certification database may also store reference data about a specific person, in particular, the person carrying the handheld device. The first option may guarantee privacy much better than the second option. Additionally, the disability certification database may be site-specific. The disability certification database may only be implemented for one specific site or, the disability certification database may serve a plurality of sites. Such an implementation may be controlled by a government agency or a private institution. A central implementation may have the advantage that, e.g., all public, but also private buildings may be supported with the same infrastructure which may reduce cost and increase the usability of the building by persons having a disability.

According to one optional embodiment, the method may also comprise receiving, by the handheld device, site-specific and disability code dependent navigation data. Thus, a smart phone, tablet computer, or smart watch may receive the direction data for an in-building navigation. It may be noted that typically GPS data (global positioning system data) may not be available inside buildings. Thus, the handheld device may receive the location data inside the building via Bluetooth® or WiFi (WLAN) landmarks or beacons and may use triangulation for an exact positioning. The navigation data may also comprise a complete map of the inside of the actual building (or the site).

According to one permissive embodiment, the method may also comprise pushing an application to the handheld device, upon transmitting the disability code from the handheld device to the sensor. Thus, after the sensor receives a code, a controller at the site or building may receive the disability code from the handheld device, and the controller may be enabled to transmit an application or smart-device app to the handheld device. This may be any information regarding the building or site, like direction data, general information or event specific data at the site, like a museum. The handheld device may receive the data only, or optionally also the app for an interpretation of the data.

According to embodiments of the method, the facilities may comprise an elevator, a door or a pathway, e.g., to be used only by disabled people, an alarm signal, e.g., dedicated to support personnel of the site, a facility for fast lanes so that disabled people do not have to wait in a queue (such as at a large venue or entertainment venue), an activation signal for an automatic door, and any other equipment useful for making a usage of the site easier for a person with a disability.

According to one advantageous embodiment of the method, the transmitting and the receiving may be based on communication technologies used in mobile telephone communication, WiFi, NFC, Bluetooth® or, optical signals. The optical signals may be from the visible or invisible spectrum (e.g. Infrared).

According to one additionally advantageous embodiment, the disability certification database may be operated by a trusted data center. Because disability information is sensitive personal data, an operation by a trusted database operator may protect privacy of the persons having the disability. Hence, using the disability code may not let outsiders—like the operators of the site—know about a certain disability of a specific person. If the disability code may be received by the sensor of the site in an encrypted form and transferred to the disability certification database, the controller of the site may only receive back requirement data for a certain person entering the site. These requirement data may be translated to actuator signals for the in-site facilities.

In the following, a detailed description of the figures will be given. All instructions in the figures are schematic. Firstly, a block diagram of an embodiment of the inventive computer implemented method for supporting a person at a site is given. Afterwards, further embodiments, as well as embodiments of the system for supporting a person at a site, and examples, will be described.

FIG. 1 shows a block diagram of an embodiment of the computer implemented method 100 for supporting a person at a site, the person having a requirement, which can include a disability, or a requirement for a disability. The requirement could be a plurality of needs, facilitations, or special treatment when receiving medical attention. Such requirements or needs can pertain to food allergies, medication allergies, medications or medical history, or requirements pertaining to physiological needs of a person, such as stress disorders. Further, requirements can include: access to facilities or locations, services, preferences, a disability or a handicap, or services or accommodations pertaining to a disability or condition, or other types or examples of particular or specified needs, conditions, or preferences, at a site, venue, facility, or location.

Also, the present disclosure can be applied to preferences of a person, not related to a physical or physiological need. For example, in an environment where user preferences, amenities, or services, are to be administered at a venue, such as a club, restaurant, or an event. Such preferences or requirements can include paid for services at a venue. For example, a venue with a large gathering of people and different levels of service or different services are purchased, possibly beforehand, such as different seating arrangements, or participation levels, or service levels.

The method 100 comprises storing, 102, a requirement code in a handheld device, and storing, 104, the requirement code and at least one characteristic relating to the requirement code in a requirement certification database which may be accessible remotely. The requirement code may be received by the handheld device by registering with the requirement certification database.

The method may further comprise, transmitting, 106, the requirement code from the handheld device to a sensor at the site. The sensor or receiver may be located at the site, e.g., in the building or outside of the building. The communication may be performed using mobile phone technologies and protocols or, WiFi or, Bluetooth® or, NFC or, IR technologies.

Finally, the method comprises receiving, 108, action data by at least one facility of the site—via a site controller—from the requirement certification database, the action data being indicative of an action to be performed by the facility dependent on the requirement code and the at least one characteristic such that the facility adapts its function to a requirement of the person having the requirement. The site may be equipped with a transceiver for sending and receiving data to/from a datacenter operating the requirement certification database, which in one embodiment can include a disability certification database having a stored disability code and the handheld device having a disability code.

FIG. 2 shows a block diagram 200 of an embodiment of a set-up of involved components. The person with a requirement (which in one example may include a disability) may be represented by the handheld device 202. It may be a wireless communication with the requirement certification database 208 which may be operated remotely by a trusted data center (not shown). When approaching the site 204—e.g., a place, a building a combination of it or any other public or non-public site—it may be equipped with a sensor 206 (which may also be a part of a transceiver). The sensor 206 may be outside of the building—e.g., near the entrance—or inside the building. Additionally, a plurality of sensors may be spread across the site. The signals of the sensors 206 may be processed by the site controller 216 which may also be connected to a plurality of facilities 214 within the site 204. These facilities 214 may be elevators, doors, fast lane arrangements or, any other technical and non-technical equipment instrumental to ease the usage of the site and its functions by the person having the requirement.

It may be noted that the person with a requirement, such as a disability, may have the choice to activate the sending of the requirement code from the handheld device 202 to the sensor 206 or not. In one instance, a person may—under certain circumstances—not want to be identified as a person needing attention or having particular needs. In this case, no disability code may be sent for a person and he/she may enter the site as any other visitor. Furthermore, the handheld device may send the disability code upfront to coming near the site so that the staff of the site may prepare to respond to requirements of a person's needs.

The controller 216 may also be connected to the requirement certification database 208 in order to receive action data required to control the facilities 214 in a way useful for the person having the requirement. The controller 216 for local processing at the site may also have access to app repository 210 for storing applications for mobile devices, like, e.g., the handheld device 202. This may include in-side or in-house navigation applications using in-house beacons for an orientation in places without GPS data. Thus, the controller 216 may receive the app from the repository 210 and may send it wirelessly to the handheld device 202. The app repository 210 may be a site-specific database operated at the site 204; alternatively, the repository 210 may be operated and managed by the same data center operating the requirement certification database 208.

If privacy and security allows, the requirement certification database 208 may also store the history of entering sites having the required equipment to support the person with the requirement. All of the data may be added to a requirement record of a specific person.

Furthermore, the controller 216 may have access to a local notification database. An alert may be activatable, e.g., in case of a wrong or unknown requirement code. A personal assistant may be notified by the controller and the site-specific downloads to the handheld device may be started. The controller 216 may also be adapted for detecting that a person with a requirement has left the site. Furthermore, the controller may record all used facilities and time data about the visit in statistical form in order to improve the services delivered by the site over time.

The controller may also be connected to a local notification database 212 recording an entering of a person with a requirement to the site. If privacy and security rules allow, the local notification database 212 may record interaction of the person with the facilities of the building and the services required and used. In this way, the service provided to a visitor having requirements may be improved over time.

FIG. 3 shows a block diagram of an embodiment of the system 300 for supporting a person at a site, the person having a requirement in an overview style. The system 300 comprises a handheld device 202 adapted for storing a requirement code, a requirement certification database unit 302 adapted for storing the requirement code and at least one characteristic relating to the requirement code, a sensor 206 at the site adapted for receiving the requirement code from the handheld device 202, and a receiver 304 adapted for receiving action data by a facility of the site from the requirement certification database, the action data being indicative of an action to be performed by the facility dependent on the requirement code and the at least one characteristic such that the facility adapts its function to a requirement of the person having the requirement.

Embodiments of the invention may be implemented together with virtually any type of computer, regardless of the platform being suitable for storing and/or executing program code. FIG. 4 shows, as an example, a computing system 400 suitable for executing program code related to the proposed method.

The computing system 400 is only one example of a suitable computer system and is not intended to suggest any limitation as to the scope of use or functionality of embodiments of the invention described herein. Regardless, computer system/server 400 is capable of being implemented and/or performing any of the functionality set forth hereinabove. In the computer system 400, there are components, which are operational with numerous other general purpose or special purpose computing system environments or configurations. Examples of well-known computing systems, environments, and/or configurations that may be suitable for use with computer system/server 400 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 400 may be described in the general context of computer system-executable instructions, such as program modules, being executed by a computer system 400. Generally, program modules may include routines, programs, objects, components, logic, data structures, and so on that perform particular tasks or implement particular abstract data types. Computer system/server 400 may be practiced in distributed cloud computing environments where tasks are performed by remote processing devices that are linked through a communications network. In a distributed cloud computing environment, program modules may be located in both local and remote computer system storage media including memory storage devices.

As shown in the figure, computer system/server 400 is shown in the form of a general-purpose computing device. The components of computer system/server 400 may include, but are not limited to, one or more processors or processing units 402, a system memory 404, and a bus 406 that couples various system components including system memory 404 to the processor 402. Bus 406 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 400 typically includes a variety of computer system readable media. Such media may be any available media that is accessible by computer system/server 400, and it includes both, volatile and non-volatile media, removable and non-removable media.

The system memory 404 may include computer system readable media in the form of volatile memory, such as random access memory (RAM) 408 and/or cache memory 410. Computer system/server 400 may further include other removable/non-removable, volatile/non-volatile computer system storage media. By way of example only, storage system 412 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 406 by one or more data media interfaces. As will be further depicted and described below, memory 404 may include at least one program product having a set (e.g., at least one) of program modules that are configured to carry out the functions of embodiments of the invention.

The program/utility, having a set (at least one) of program modules 416, may be stored in memory 404 by way of example, and not limitation, as well as an operating system, one or more application programs, other program modules, and program data. Each of the operating system, one or more application programs, other program modules, and program data or some combination thereof, may include an implementation of a networking environment. Program modules 416 generally carry out the functions and/or methodologies of embodiments of the invention as described herein.

The computer system/server 400 may also communicate with one or more external devices 418 such as a keyboard, a pointing device, a display 420, etc.; one or more devices that enable a user to interact with computer system/server 400; and/or any devices (e.g., network card, modem, etc.) that enable computer system/server 400 to communicate with one or more other computing devices. Such communication can occur via Input/Output (I/O) interfaces 414. Still yet, computer system/server 400 may communicate with one or more networks such as a local area network (LAN), a general wide area network (WAN), and/or a public network (e.g., the Internet) via network adapter 422. As depicted, network adapter 422 may communicate with the other components of computer system/server 400 via bus 406. It should be understood that although not shown, other hardware and/or software components could be used in conjunction with computer system/server 400. Examples, include, but are not limited to: microcode, device drivers, redundant processing units, external disk drive arrays, RAID systems, tape drives, and data archival storage systems, etc.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus', and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus', or another device to cause a series of operational steps to be performed on the computer, other programmable apparatus or other device to produce a computer implemented process, such that the instructions which execute on the computer, other programmable apparatus', or another device implement the functions/acts specified in the flowchart and/or block diagram block or blocks.

The flowcharts and/or block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 5, illustrative cloud computing environment 1250 is depicted. As shown, cloud computing environment 1250 includes one or more cloud computing nodes 1210 with which local computing devices used by cloud consumers, such as, for example, personal digital assistant (PDA) or cellular telephone 1254A, desktop computer 1254B, laptop computer 1254C, and/or automobile computer system 1254N may communicate. Nodes 1210 may communicate with one another. They may be grouped (not shown) physically or virtually, in one or more networks, such as Private, Community, Public, or Hybrid clouds as described hereinabove, or a combination thereof. This allows cloud computing environment 1250 to offer infrastructure, platforms and/or software as services for which a cloud consumer does not need to maintain resources on a local computing device. It is understood that the types of computing devices 1254A-N shown in FIG. 5 are intended to be illustrative only and that computing nodes 1210 and cloud computing environment 5120 can communicate with any type of computerized device over any type of network and/or network addressable connection (e.g., using a web browser).

Referring now to FIG. 6, a set of functional abstraction layers provided by cloud computing environment 1250 (FIG. 5) is shown. It should be understood in advance that the components, layers, and functions shown in FIG. 6 are intended to be illustrative only and embodiments of the invention are not limited thereto. As depicted, the following layers and corresponding functions are provided:

Hardware and software layer 1260 includes hardware and software components. Examples of hardware components include: mainframes 1261; RISC (Reduced Instruction Set Computer) architecture based servers 1262; servers 1263; blade servers 1264; storage devices 1265; and networks and networking components 1266. In some embodiments, software components include network application server software 1267 and database software 1268.

Virtualization layer 1270 provides an abstraction layer from which the following examples of virtual entities may be provided: virtual servers 1271; virtual storage 1272; virtual networks 1273, including virtual private networks; virtual applications and operating systems 1274; and virtual clients 1275.

In one example, management layer 1280 may provide the functions described below. Resource provisioning 1281 provides dynamic procurement of computing resources and other resources that are utilized to perform tasks within the cloud computing environment. Metering and Pricing 1282 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 1283 provides access to the cloud computing environment for consumers and system administrators. Service level management 1284 provides cloud computing resource allocation and management such that required service levels are met. Service Level Agreement (SLA) planning and fulfillment 1285 provide pre-arrangement for, and procurement of, cloud computing resources for which a future requirement is anticipated in accordance with an SLA.

Workloads layer 1290 provides examples of functionality for which the cloud computing environment may be utilized. Examples of workloads and functions which may be provided from this layer include: mapping and navigation 1291; software development and lifecycle management 1292; virtual classroom education delivery 1293; data analytics processing 1294; transaction processing 1295; and analyzing data and providing a recommended action for supporting a person at a site 1296.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A computer implemented method for supporting a person at a site where the person has one or more requirements when visiting the site, the method comprising:

storing a requirement code in a handheld device, wherein the handheld device is selected from a group consisting of: a smartphone, a smartwatch, a tablet computer, a dedicated disability system, smart glasses, and a smart bracelet;

storing the requirement code and at least one characteristic relating to the requirement code in a requirement certification database, wherein the requirement certification database stores action data for one or more sites, and the requirement certification database is operated by a trusted data center, the trusted data center operating under special conditions including data security and privacy conditions;

transmitting the requirement code from the handheld device to a sensor at a site where a person has a requirement, corresponding to the requirement code, when visiting the site, wherein the transmitting and the receiving is based on communication technology used in one or more of: mobile telephone communication, WLAN, NFC, Bluetooth®, or, optical signals;

receiving action data by a facility of the site from the requirement certification database, the action data being indicative of an action to be performed by the facility dependent on the requirement code and the at least one characteristic such that the facility adapts its function to the requirement of the person;

receiving action data required to control facilities in a useful way for the person having the requirement, using a controller connected to the requirement certification database, the controller being for local processing at the site, and the controller communicating with an application repository for storing applications for the handheld device, applications including inside or in-house navigation applications using in-house beacons for orienting the person in places within the site without GPS data, the controller receiving an application from the repository and sending the application wirelessly to the handheld device, the application repository being a site-specific database operated at the site, or operated and managed by the trusted data center;

based on privacy and security rules, the requirement certification database storing a history of entering sites having a required equipment to support the person with the requirement, wherein history data including the stored history is added to a requirement record of a specific person;

accessing a local notification database by the controller, activating an alert when a wrong or unknown requirement code is received, and based on a wrong or unknown requirement code being received, notifying, by the controller, a personal assistant;

detecting, by the controller, when the person with the requirement has left the site;

recording, by the controller, all used facilities by the person and time data about the visit in statistical form, in order to improve the services delivered by the site over time;

connecting the controller to a local notification database, recording an entering of the person with the requirement to the site; and based on privacy and security rules, the local notification database recording interaction of the person with the facilities of the building and the services required and used, in order to improve services provided to the person having the requirement over time.

* * * * *